United States Patent [19]

Toja et al.

[11] Patent Number: 4,810,722

[45] Date of Patent: Mar. 7, 1989

[54] 1-STYRENESULPHONYL-2-OXO-5-HYDROXY PYRROLIDINES AND THEIR USE FOR MEMORY RESTORATION AFTER ELECTOSHOCK TREATMENT

[75] Inventors: Emilio Toja, Milan; Carlo Zirotti, Arona; Giulio Galliani; Fernando Barzaghi, both of Monza, all of Italy

[73] Assignee: Roussel Uclaf, Paris, France

[21] Appl. No.: 30,113

[22] Filed: Mar. 26, 1987

[30] Foreign Application Priority Data

Mar. 28, 1986 [IT] Italy .................. 19916 A/86

[51] Int. Cl.⁴ .................. A61K 31/40; C07D 207/48
[52] U.S. Cl. .................. 514/425; 548/542
[58] Field of Search .................. 548/542; 514/425

[56] References Cited

U.S. PATENT DOCUMENTS 3,423,426  1/1969  Kuhn .................. 548/542
3,686,169  8/1972  Coran et al. .................. 548/542

FOREIGN PATENT DOCUMENTS 0138721  4/1985  European Pat. Off. .

OTHER PUBLICATIONS

Drugs of the Future, vol. 10, No. 12, 1985, pp. 972, 974.

Primary Examiner—David B. Springer

Attorney, Agent, or Firm—Stevens, Davis, Miller & Mosher

[57] ABSTRACT

The therapeutic compounds useful in the treatment of patients suffering from intellectual or nervous asthenias, memory failures or old age and excessive intellectual fatigue having the formula (I):

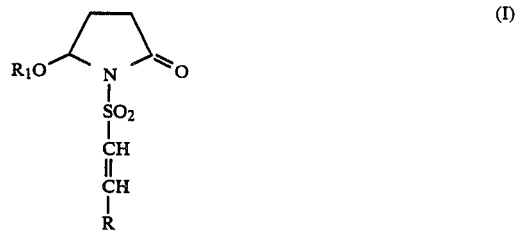

in which $R_1$ represents an alkyl radical, linear or branched, containing up to 8 carbons atoms, an acyl radical containing from 1 to 6 carbon atoms or a cycloalkyl radical containing from 3 to 6 carbon atoms and R represents an aryl radical containing up to 14 carbon atoms, unsubstituted or substituted, or a mono- or polycyclic heterocyclic radical, unsubstituted or substituted. Also, therapeutic compositions containing the compound, method of preparing the compound and method of use.

6 Claims, No Drawings

1-STYRENESULPHONYL-2-OXO-5-HYDROXY PYRROLIDINES AND THEIR USE FOR MEMORY RESTORATION AFTER ELECTOSHOCK TREATMENT

BACKGROUND OF THE INVENTION

The invention is concerned with new derivatives of 1-styrene-sulphonyl-2-oxo-5-hydroxy pyrrolidine, the process and the intermediates for their preparation, their use as medicaments and compositions containing them.

The invention relates to compounds of the general formulas (I):

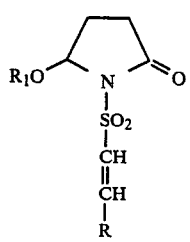

(I)

in which $R_1$ represents a linear or branched alkyl radical, containing up to 8 carbon atoms, an acyl radical containing from 1 to 6 carbon atoms or a cycloalkyl radical containing from 3 to 6 carbon atoms and R represents an aryl radical containing up to 14 carbon atoms, possibly substituted, or a heterocyclic radical, mono- or polycyclic, possibly substituted.

The invention includes the compounds with the formula (I) in which the geometry of the double bond is trans or cis, as well as mixtures of these products with trans and cis geometry.

By alkyl radical, there is preferably meant an alkyl radical containing from 1 to 5 carbon atoms, for example, a methyl, ethyl, n-propyl, isopropyl, n-butyl, isobutyl, tertbutyl or n-pentyl radical.

By acyl radical, there is preferably meant an acetyl, propionyl or butyryl radical.

By cycloalkyl radical, there is preferably meant a cyclopropyl, cyclobutyl, cyclopentyl or cyclohexyl radical.

By aryl radical, there is preferably meant a phenyl or naphthyl radical.

By heterocyclic radical, there is preferably meant one of the following radicals; furyl, thienyl, pyranyl, pyridyl, benzofuranyl, isobenzofuranyl, chromanyl, isochromanyl, chromenyl, xanthenyl, phenoxathienyl, oxazolyl, isoxazolyl, furazanyl, phenoxazinyl, thieno(2,3-b)furanyl, 2H-furo(3,2-b)pyranyl, benzoxazolyl or morpholinyl.

When the radical R is substituted, it is preferably carries as substituents one or more substituents selected from the group consisting of the free, esterified or etherified hydroxyl radicals, in which the ester or ether part contains from 1 to 18 carbon atoms, such, for example as the acetoxy radical, the methoxy radical or the benzyloxy radical; the radical

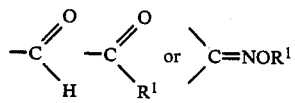

in which $R^1$ represents an alkyl radical containing 1 to 8 carbon atoms; the linear, branched or cyclized, saturated or unsaturated alkyl radicals, containing up to 18 carbon atoms, such, for example, as the methyl, ethyl, propyl or isopropyl radical; the ethenyl radical, or the ethynyl radical; the halogen atoms, such as fluorine, chlorine, bromine; the $CF_3$, $SCF_3$, $OCF_3$, $NO_2$, $NH_2$ or $C\equiv N$ groups; and the phenyl radical.

The invention particularly relates to the compounds of the formula (I) in which R represents a phenyl radical possibly substituted by an alkoxy radical containing up to 4 carbon atoms, such, for example as the methoxy radical.

More particularly, the invention has as its object the compounds with the formula (I) in which $R_1$ represents an ethyl radical.

Even more particularly an object of the invention are the products of the examples.

The compounds of the invention possess useful pharmacological properties; they retard the extinction of a conditioned avoidance response, they retard the disappearance of a learned response and they benefit attention, vigilance and memorization.

Therefore, the products with the formula (I) are useful in particular in the treatment of intellectual or nervous asthenias, memory failures, old age and excessive intellectual fatigue.

The invention has more particularly, as an object as a medicament, the product of Example 1.

The usual posology is variable according to the affection concerned, the subject treated and the administration route, it can be between 50 mg and 3000 mg per day, preferably from 100 to 600 mg, for example between 150 and 1500 mg per day, preferably between 100 and 200 mg, in one or more doses for the product of Example 1 administered by oral route.

The present invention also relates to the pharmaceutical compositions containing as the active principle at least one compound with the formula (I). The pharmaceutical compositions of the invention can be solid or liquid and are presented in the pharmaceutical forms currently use in human medicine, such, for example, as plain or sugar-coated tablets, capsules, granules, suppositories or injectable preparations; they are prepared according to the usual methods.

The active principle or principles can be incorporated with the excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The invention also has as its object a process for the preparation of the compounds with the formula (I) characterized in that a compound with the formula (II):

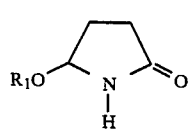

(II)

in which $R_1$ has the same significance as discussed previously, is submitted to the action of a compound with the formula (III):

$$RCH=CH-SO_2Hal \quad (III)$$

in which Hal represents a chlorine or bromine atom and R has the same significance as discussed previously, in order to obtain the corresponding compound with the formula (I).

In a preferred way of carrying out the process of the invention, the reaction between the product with the formula (II) and the product with the formula (III) is effectuated:

(a) in the presence of a strong base such as butyllithium or an alkaline hydride, such as sodium hydride, (b) in a solvent chosen from the group constituted by tetrahydrofuran, benzene, dimethylformamide, dimethylsulphoxide, the monoethyl ether of diethylene glycol and the diethyl ether of diethylene glycol.

The products with the formula (II) used as starting products are products known in a general way, and they can be prepared according to the processes described in TETRAHEDRON 31, 1437 (1975), TETRAHEDRON 41, 2007 (1985) or in SYNTHESIS (4) 315-17 (1980).

The 5-n-propyloxy pyrrolidine-2-one and the 5-isopropyloxy pyrrolidine-2-one, however, are new products and are themselves one of the subjects of the present invention.

The products with the formnula (III), used as starting products are known in a general way; they can be prepared according to the process described in CA 47 3262c (1953).

The 4-methoxystyrene sulphonyl chloride is, however, a new product and is, therefore for this reason, a subject of the present invention.

The following examples illustrate the invention without, however, limiting it.

EXAMPLE 1

1-(styrenesulphonyl)-2-oxo-5-ethoxy pyrrolidine 2.6 g of 2-oxo-5-ethoxy pyrrolidine is dissolved in 80 cm³ of anhydrous tetrahydrofuran, then cooled to −5° C., and 12.6 cm³ of butyllithium is added. After 20 minutes under agitation, there is added slowly at the same temperature, 4.05 g of styrene-sulphonyl chloride (CA 47, 3262c (1953)) in 10 cm³ of tetrahydrofuran. After allowing this to return to ambient temperature, after 4 hours, it is concentrated to dryness and the residue is chromatographed on silica. 1.3 g of the expected product is obtained, which is crystallized from a mixture of ethyl ether and hexane. m.p.=61°-63° C.

| Analysis: $C_{14}H_{17}NO_4S$ | | | | | | | |
|---|---|---|---|---|---|---|---|
| Calculated: | C % | 56.93 | H % | 5.8 | N % | 4.74 |
| Found: | | 56.85 | | 5.63 | | 4.57 |

EXAMPLE 2

1-(4-methoxystyrenesulphonyl)-2-oxo-5-ethoxy pyrrolidine 2.2 g of 2-oxo-5-ethoxy pyrrolidine is dissolved in 170 cm³ of anhydrous tetrahydrofuran, then, under an inert gas, at −10° to −15° C., 10.6 cm³ of 1.6M solution of butyllithium in hexane is added. After 30 minutes, 4.1 g of 4-methoxystyrenesulphonyl is added slowly, the whole is allowed to return slowly to ambient temperature and concentrated to dryness. The residue is chromatographed on silica, and 1.5 g of product is obtained which is recrystallized from isopropanol. 1.15 g of the expected product is obtained, m.p.=134°-136° C.

| Analysis $C_{15}H_{19}NO_5S$ | | | | | | |
|---|---|---|---|---|---|---|
| Calculated: | C % | 55.36 | H % | 5.89 | N % | 4.30 |
| Found: | | 55.24 | | 5.83 | | 4.16 |

Preparation of the 4-methoxystyrenesulphonyl chloride.

A mixture of 5.5 g of paramethoxy styrene, 13 g of SO₃-pyridine and 5 cm³ of dichloroethane is heated to 110° C. for 9 hours 30 minutes in an enclosure. After cooling, it is diluted in methylene chloride and then concentrated to dryness. 7.6 g of phosphorus pentachloride is added to the mixture which is heated to about 85° C. until solution is total, and then for 3 hours at 45° C. It is then concentrated to dryness, poured on to a water-ice mixture, extracted with chloroform, dried and concentrated to dryness. The mixture is then chromatographed rapidly on silica, elu,ting with a hexane-chloroform (1—1) mixture. A product is obtained (m.p. 65°-67° C.) which is then crystallized from a hexane-chloroform mixture while cooling for 40 minutes. 3.4 g of the expected product is obtained, m.p.=73°-74° C.

EXAMPLE 3

1-(styrenesulphonyl)-2-oxo-5-methoxy pyrrolidine 3.29 g of 5-methoxy-2-oxo pyrrolidine (SYNTHESIS 4, 315-17 (1980)) is dissolved in 100 cm³ of anhydrous tetrahydrofuran. After cooling to −20° C. 17.86 cm³ of a 1.6M solution of N-butyllithium in hexane is a while keeping the temperature at about −30° C. The mixture is agitated for 30 minutes at −35° to −30° C., then a solution of 5.80 g of styrenesulphonyl chloride (CA 47, 3262c, 1953) in 14 cm³ of anhydrous tetrahydrofuran is added slowly. After allowing this to return to ambient temperature, the solvent is evaporated under reduced pressure, and the residue is chromatographed on silica gel, eluting with a mixture of ethyl acetate and n-hexane (1—). The product obtained is crystallized from isopropanol, and 3 g of the expected product is obtained. m.p. 98°-99° C.

| Analysis: $C_{13}H_{15}NO_4S$ | | | | | | |
|---|---|---|---|---|---|---|
| Calculated: | C % | 55.50 | H % | 5.37 | N % | 4.98 |
| Found: | | 55.22 | | 5.17 | | 4.89 |

EXAMPLE 4

1-(styrenesulphonyl)-2-oxo-5-N-propoxy pyrrolidine

To a solution of 4.09 g of 2-oxo-5N-propyloxy pyrrolidine in 100 cm³ of anhydrous tetrahydrofuran, cooled to −30° C., 17.89 cm³ of 1.6M solution of N-butyllithium in hexane is added, operating at −30° to −15° C. This is agitated for 30 minutes at −30° C., then a solution of 5.8 g of styrenesulphonyl chloride in 14 cm³ of tetrahydrofuran (CA 47, 3262c, 1953) is added slowly. After allowing to return to ambient temperature, the solvent is evaporated off under reduced pressure and the residue is chromatographed on silica gel, eluting with a mixture of ethyl acetate and n-hexane (1—1). The residue is crystallized from isopropanol, and 3 g of the expected product is obtained. m.p. 74°-75° C.

| Analysis: $C_{15}H_{19}NO_4S$ (309.40) | | | | | |
|---|---|---|---|---|---|
| Calculated: | C % | 58.23 | H % | 6.19 | N % | 4.53 |
| Found: | | 58.35 | | 6.18 | | 4.49 |

Preparation of the 2-oxo-5-n-propyloxy pyrrolidine.

To a mixture of 28.64 g of succinimide and of 1200 cm³ of N-propanol, cooled to −7° C., 7 g of sodium bobohydride is added. This is agitated for 4 hours at −7° to 0° C., while adding every 15 minutes 15 drops of a 2N solution of hydrochloric acid in N-propanol. The mixture is then taken to a pH of about 2 by adding a 2N solution of hydrochloric acid in N-propanol, agitated for 1 hour at about 0° C., then returned to pH 7 by the addition of a saturated solution of potassium hydroxide in N-propanol. After allowing a return to ambient temperature, the solvent is evaporated off under reduced pressure. The residue is extracted with 550 cm³ of chloroform, filtered, the organic solution is washed with water, dried and the solvent is evaporated under reduced pressure. 27.5 g of the expected product is obtained. m.p. 52°–54° C.

EXAMPLE 5

1-(styrenesulphonyl)-2-oxo-5-isopropyloxy pyrrolidine

To a solution of 3.53 g of 2-oxo-5-isopropyloxy pyrrolidine in 85 cm³ of anhydrous tetrahydrofuran, cooled to −10° C., 15.42 g of a 1.6M solution of N-butyllithium in hexane is added, operating at −10° to −5° C. This is agitated for 30 minutes, while cooling to −45° C., then a solution of 5 g of styrenesulphonyl chloride (CA 47, 3262c, 1953) in 35 cm³ of anhydrous tetrahydrofuran is added slowly, while operating at −45° to −40° C. After allowing a return to ambient temperature, the solvent is evaporated off under reduced pressure and the residue is chromatographed on silica, eluting with a mixture of ethyl ethyl acetate and hexane (1—1). The product obtained is crystallized from ethanol, and 3.1 g of the expected product is obtained. m.p. 92°–94° C.

| Analysis: $C_{15}H_{19}NO_4S$ | | | | | |
|---|---|---|---|---|---|
| Calculated: | C % | 58.23 | H % | 6.19 | N % | 4.53 |
| Found: | | 58.04 | | 6.07 | | 4.42 |

Preparation of the 2-oxo-5-isopropyloxy pyrrolidine.

To a mixture of 28.64 g of succinimide in 1200 cm³ of isopropanol cooled to −10° C., 32.8 g of sodium borohydride is added, with agitaton for 4 hours, while maintaining the temperature at −10° to 0° C. Every 15 minutes 15 drops of a 2M solution of hydrochloric acid in isopropanol is added. Operating at 0° to +2° C., the reactional mixture is then taken to pH 2-3 by the addition of a 2N solution of hydrochloric acid in isopropanol, then agitated for 2 hours at the same temperature. Neutralization is then done by the addition of a saturated solution of potassium hydroxide in isopropanol, operating at −°C. The isopropanol is evaporated off under reduced pressure, and after extracting with chloroform, filtering and evaporating off the solvent under reduced pressure, 20.5 g of the expected product is obtained, m.p. 68° to 71° C.

EXAMPLE 6

1-(4-nitrostyrenesulphonyl)-2-oxo-5-ethoxy pyrrolidine 3.25 g of 5-ethoxy pyrrolidin-2-one is dissolved in 100 cm³ of anhydrous tetrahydrofuran and, at −25° C., under agitation, 16.25 cm³ of butyllithium at 15% in hexane is added. After 15 minutes under agitation, at −30° C., 6.1 g of beta-4-nitrostyrenesulphonyl (J. Am. Chem. Soc. 68, 1778, 1946), dissolved in 100 cm³ of tetrahydrofuran is added. After 2 hours, the mixture is allowed to return to ambient temperature, then concentrated to dryness; water is added and it is made to crystallize. The crystals are filtered off, dried and chromatographed on silica, eluting with a mixture of toluene and ethyl acetate (8-2). 2.7 g of the expected product is obtained which is crystallized from isopropanol. 2.4 g of product is obtained, m.p. 162°–163° C.

| Analysis: $C_{14}H_{16}N_2O_6S$: 340.36 | | | | | |
|---|---|---|---|---|---|
| Calculated: | C % | 49.40 | H % | 4.74 | N % | 8.23 |
| Found: | | 48.93 | | 4.72 | | 8.08 |

EXAMPLE 7

1-(4-methoxystyrenesulphonyl)-2-oxo-5-isopropoxy pyrrolidine 2.89 of 5-isopropoxy pyrrolidin-2-one is dissolved in 100 cm³ of anhydrous tetrahydrofuran, then, under an inert gas, at −30° to −32° C., 13.4 cm³ of a 1.6M solution of butyllithium in hexane is added. After 25 minutes at −40° C., 4.7 g of beta-4-methoxy styrene sulphonyl chloride in solution in 15 cm³ of tetrahydrofuran is added slowly. After allowing a return slowly to the ambient temperature and concentrating to dryness, the residue is chromatographed on silica, eluting with a mixture of toluene and ethyl acetate (8-2). The product is recrystallized from isopropyl ether and 2.4 g of the expected product is obtained, m.p. 101°–103° C.

| Analysis: $C_{16}H_{21}NO_5S$ = 339.41 | | | | | |
|---|---|---|---|---|---|
| Calculated: | C % | 56.62 | H % | 6.23 | N % | 4.12 |
| Found: | | 56.83 | | 6.31 | | 4.21 |

EXAMPLE 8

1-(4-nitrostyrenesulphonyl)-2-oxo-5-isopropoxy pyrrolidine 3.46 g of 5-isopropoxy pyrrolidin-2-one is dissolved in 100 cm³ of anhydrous tetrahydrofuran and under agitation at −30° C., 16 cm³ of butyllithium at 15% in hexane is added. After 20 minutes, at −35° C., 6 g of beta-4-nitrostyrene sulphonyl chloride in solution in 100 cm³ of anhydrous tetrahydrofuran is added. After 2 hours, and allowing return to ambient temperature the mixture is concentrated and crystallized from isopropanol. The crystals are filtered and recrystallized from isopropanol. 3 g of the expected product is obtained. m.p. 178°–179° C.

| Analysis: $C_{15}H_{18}M_2O_6S$ = 354.396 | | | | | |
|---|---|---|---|---|---|
| Calculated: | C % | 50.84 | 8% | 5.12 | N % | 7.90 |
| Found: | | 50.66 | | 5.24 | | 7.87 |

EXAMPLE 9

1-(styrenesulphonyl)-2-oxo-pentyloxy pyrrolidine 2 g of 5-pentyloxy pyrrolidin-2-one is dissolved in 90 cm³ of anhydrous tetrahydrofuran, cooled to −30° C.

under agitation and under an inert gas. 7.7 cm³ of a 1.5M solution of butyllithium in hexane is added, and after 25 minutes there is added slowly at −40° C., 2.36 g of beta-styrene sulphonyl chloride in solution in tetrahydrofuran. After allowing return to ambient temperature, concentrating to dryness, chromatographing on silica, eluting with a mixture of toluene and ethyl acetate (8-2) and recrystallizing from isopropyl ether, 2.1 g of the expected product is obtained. m.p. 66°-68° C.

| Analysis: $C_{17}H_{25}NO_4S$: 337.44 | | | | | | | |
|---|---|---|---|---|---|---|---|
| Calculated: | C % | 60.51 | H % | 6.87 | N % | 4.15 |
| Found: | | 60.46 | | 6.79 | | 4.28 |

Using a method similar to that used in Examples 1 to 9, the following products in particular can be prepared:

1-(3-trifluoromethyl styrenesulphonyl)-2-oxo-5-ethoxy pyrrolidine, m.p. 72°-73° C., 1-(4-phenyl styrene sulphonyl)-2-oxo-5-ethoxy pyrrolidine, m.p. 132°-134° C., 1-(3-trifluoromethyl styrene sulphonyl)-2-oxo-5-isopropoxy pyrrolidine, m.p. 125°-127° C., 1-(4-phenyl styrene sulphonyl)-2-oxo-5-isopropoxy pyrrolidine, m.p. 137°-139° C.

PHARMACOLOGICAL STUDY

Acute toxicity and behavior

We used malke mice (CD₁ Charles Rivers) weighing 22-23 g, fasting for 16 hours. The products were administered normally by oral route at doses of 1000-500-250 mg/kg.

The effect of the products on the behavior of the animals was evaluated according to the method described by Irvin (Psychopharmacologia 13, 222-257, 1968) during the first 8 hours and on the 24th hour.

The mortaility was noted during the 7 days following the treatment.

The $LD_{50}$ was thus found greater than 1000 mg/kg for the products of Examples 1 to 9.

Learning and memorization

We used male mice (CD₁ Charles Rivers) weighing 25-30 g. The animals were placed in the illuminated part of a box with two compartments, communicating by an opening. (F. Barzaghi et G. Giuliani, Brit. J. Pharmacol. 86, 661, p. 1985).

At the instant when the mouse passes from the illuminated to the dark compartment, the opening closes and it is immediately punished by an electric discharge to the paws. The animal submitted to this procedure learns to memorize the punishment. In fact, if it is put back into the illuminated compartment, it will avoid crossing the opening and re-entering the dark compartment.

In order to induce a retrograde amnesia, immediately after the learning the animals are submitted to an electric shock. After the electric shock, the products are administered by oral route at doses of 12.5, 25, 50, 100 and 200 mg/kg.

We used from 10 to 30 animals per dose.

The anti-amnesic effect of the products is evaluated 3 hours after the treatment, using the same system as that used for the acquisition.

The time taken by the animals to return into the dark compartment (time limit 180 seconds) is used as evaluation parameter.

In our experimental conditions, the control animals entered with a latency time of 40-50 seconds.

The results are expressed as a percentage of the increase of the latency time as compared with that of the corresponding controls.

The following are the results:

| Product of Example | Percentage of Increase of Latency Time As Compared With the Controls | | | | |
|---|---|---|---|---|---|
| | DOSE:mg/kg:os | | | | |
| | 200 | 100 | 50 | 25 | 12.5 |
| 1 | +108* | +110* | +91* | +50* | +19* |
| 2 | +50* | +20 | +14 | +14 | — |
| 3 | +102* | +47 | +12 | +21 | — |
| 4 | +103* | +103* | +50* | +29 | — |
| 5 | +130* | +98* | +66* | +22 | — |
| 7 | +68* | +40* | — | — | — |
| 8 | +49* | +53* | +29 | +23 | — |
| 9 | +57* | +60* | +39 | +27 | +9 |
| pyracetam | +20 | +48* | +10 | +19 | — |
| antracetam | +32 | +88* | +77* | +39 | — |

+Values notably different in comparison with controls.

The products of Examples 1 to 5 and 7 to 9 are shown to be active. In particular, the product of Example 1 improves in a significant way the behavior of the animals at a dose one-half that of antracetam. Furthermore, the range of effective doses is larger than in the case of antracetam.

Examples of Pharmaceutical Compositions (A) Tablets have been prepared having the following formula:

Product of Example 1: 100 mg

Excipient q.s. for a tablet finished at: 300 mg (Detail of excipient; lactose, corn starch, treated starch, rice starch, magnesium stearate, talc).

(B) Gelules have been prepared having the following formula:

Product of Example 1: 200 mg

Excipient q.s. for a gelule finished at: 300 mg (Detail of excipient; talc, magnesium stearate, aerosil).

We claim:

1. A compound of the formula (I)

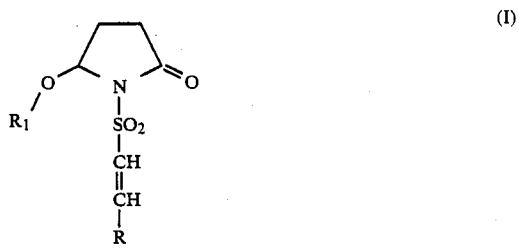

in which $R_1$ represents an alkyl radical, linear or branched, containing up to 8 carbon atoms, an alkanoyl radical containing from 1 to 6 carbon atoms or a cycloalkyl radical containing from 3 to 6 carbon atoms and R is selected from the group consisting of phenyl, unsubstituted or substituted by alkoxy containing up to 4 carbon atoms, $NO_2$, $CF_3$, or phenyl.

2. Compounds of the formula (I) as defined in claim 1, in which R represents a phenyl radical, unsubstituted or substituted by an alkoxy radical containing up to 4 carbon atoms.

3. Compounds as defined in claim 1 or 2, in which $R_1$ represents an ethyl radical.

4. A compound as defined in claim 3, which is 1-(styrene sulphonyl)-2-oxo-5-ethoxy pyrrolidine.

5. A pharmaceutical composition comprising a compound as defined in claim 1 and a pharmaceutically acceptable carrier therefor.

6. A method of restoration of memory loss after electroshock treatment comprising administering to the subject an amount effective to restore the memory loss of a compound as defined in claim 1.

* * * * *